United States Patent [19]

Willett

[11] Patent Number: 5,026,362

[45] Date of Patent: Jun. 25, 1991

[54] OSTOMY BAG HOLDER AND COVER

[76] Inventor: Elsie M. Willett, 1641 Jeanette St., Abilene, Tex. 79602

[21] Appl. No.: 531,770

[22] Filed: Jun. 1, 1990

Related U.S. Application Data

[63] Continuation of Ser. No. 253,485, Oct. 5, 1988, abandoned.

[51] Int. Cl.$^5$ .............................................. A61F 5/44
[52] U.S. Cl. ................................... 604/345; 604/332
[58] Field of Search ................ 604/327, 328, 331–345; 224/226, 224; 383/7

[56] References Cited

U.S. PATENT DOCUMENTS

| | | | |
|---|---|---|---|
| 2,595,934 | 5/1952 | Ginsburg | 604/342 |
| 2,662,525 | 12/1953 | Priebe | 604/332 |
| 2,688,327 | 9/1954 | Berg | 128/283 |
| 2,813,530 | 11/1956 | Nunn | 604/332 |
| 3,532,092 | 10/1970 | Rodgers | 604/343 |
| 3,897,785 | 8/1975 | Barto, Jr. | 128/295 |
| 4,173,979 | 11/1979 | Odis | 128/295 |
| 4,331,148 | 5/1982 | Steer et al. | 604/333 |
| 4,387,726 | 6/1983 | Denard | 128/760 |
| 4,439,191 | 3/1984 | Hogan | 604/332 |
| 4,495,662 | 1/1985 | Miller | 2/211 |
| 4,511,358 | 4/1985 | Johnson, Jr. et al. | 604/327 |
| 4,519,797 | 5/1985 | Hall | 604/332 |
| 4,705,512 | 11/1987 | Faucher | 604/332 |

FOREIGN PATENT DOCUMENTS

| | | | |
|---|---|---|---|
| 2722445 | 11/1978 | Fed. Rep. of Germany | 604/345 |
| 0620541 | 11/1959 | Italy | 604/338 |
| 0799986 | 8/1958 | United Kingdom | 604/344 |

*Primary Examiner*—John D. Yasko
*Assistant Examiner*—A. Gatowski
*Attorney, Agent, or Firm*—Kimmel, Crowell & Weaver

[57] ABSTRACT

An ostomy bag holder and cover of lightweight fabric material, comprises a waist encircling belt adapted to be adjustably secured about the waist of the user, and a pouch secured to the belt for holding and covering an ostomy bag, said pouch comprising a back panel having a cut-out therein for providing access from an ostomy bag to a stoma, and a front panel having releasable fastening means thereon for releasably attaching the front panel to the belt for covering an ostomy bag supported in the pouch. The front and back panels define a pocket at their lower ends for supporting the ostomy bag.

1 Claim, 2 Drawing Sheets

5,026,362

OSTOMY BAG HOLDER AND COVER

This is a continuation of application Ser. No. 253,485, filed Oct. 5, 1988, which is now abandoned.

FIELD OF THE INVENTION

This invention relates in general to ostomy bags, and more particularly, to a cover and support for an ostomy bag.

DESCRIPTION OF THE PRIOR ART

Because of disease or other pathological conditions, or due to inflammation or surgery, portions or all of a person's intestines are sometimes rendered temporarily or permanently inoperative. In these instances, a surgical procedure known as an ostomy is performed, in which a passageway or stoma is made through the stomach wall and skin, typically through the abdominal wall. A portion of the intestine is re-routed and surgically connected to the stoma such that waste material can exit the body.

As used herein, "ostomy" is intended to cover all types of surgical procedures wherein a passageway is formed through the skin and a portion of the intestine is connected thereto. If the large intestine or colon is connected to the passageway, the procedure is known as a "colostomy". When the small intestine is involved, the procedure is known as an "ileostomy". Both of these procedures require use of an ostomy bag which is worn on the body of the user and is in communication with the stoma to collect waste emitted by the body. A wide variety of ostomy bags and supports therefor have been devised in the prior art.

One type of ostomy bag in widespread use is formed of a plastic material and has an aperture located on one side for attachment to the stoma. The bag may be supported on the skin of the user and made removable so that it can be emptied when necessary. These bags are generally transparent, thus rendering the contents visible. Furthermore, the plastic material tends to stick to the skin of the user, making it uncomfortable to use.

Covers have been designed to enclose or at least partially enclose the ostomy bag, thereby obscuring the contents and providing a buffer between the plastic material of the bag and the skin of the user. Some of these covers simply fold over portions of the user's clothing, or utilize various straps and attachments for supporting them on the body of the user. Others are relatively difficult to manipulate, requiring considerable effort to remove and replace the ostomy bag. Still others are cumbersome and uncomfortable to wear, and/or are expensive to make, leading to increased cost to the user.

Examples of some prior art ostomy bag holders are shown in the following U.S. Pat. Nos.: 2,688,327, 3,897,785, 4,173,979, 4,387,726, 4,439,191, 4,495,662, 4,511,358, 4,519,797 and 4,705,512.

It would therefore be desirable to provide an ostomy bag holder and cover which not only supports the ostomy bag and covers it, but which is also relatively inexpensive and easy to use and which overcomes the other problems noted above with respect to prior art ostomy bag covers.

SUMMARY OF THE INVENTION

Accordingly, it is an object of this invention to provide an ostomy bag cover and support which is simple and lightweight in construction and which is comfortable to wear.

Another object is to provide an ostomy bag cover and support which is easy to use and which is readily adjustable to fit different size persons.

A further object of the invention is to provide an ostomy bag cover and support which has quick release attachments for securing the cover to the body of the user and for releasably supporting the ostomy bag.

These objects of the invention are accomplished by the ostomy bag cover and support of the invention, wherein a waist-encircling loop or belt has velcro fasteners or similar quick release fasteners at opposite ends thereof for adjustably securing the belt around the waist of the user. A pouch or cover is attached to the belt for holding and covering an ostomy bag and includes a rear panel having one end stitched or otherwise suitably joined to the belt, and a front panel having a lower end portion stitched or otherwise suitably joined to a lower end portion of the rear panel for forming a shallow pocket. The other end of the front panel has quick release fasteners such as velcro patches or the like for releasable attachment to similar means on the belt, whereby the front panel may be quickly and easily attached to and removed from the belt to define a sling for holding the ostomy bag. A cut-out in the rear panel provides access of the ostomy bag to the stoma.

BRIEF DESCRIPTION OF THE DRAWINGS

The foregoing and other objects and advantages of the invention will become apparent from the following detailed description and claims when considered in conjunction with the accompanying drawings, in which like reference characters designate like parts throughout the several views, and wherein:

DETAILED DESCRIPTION OF THE PREFERRED EMBODIMENTS

Figure 1:
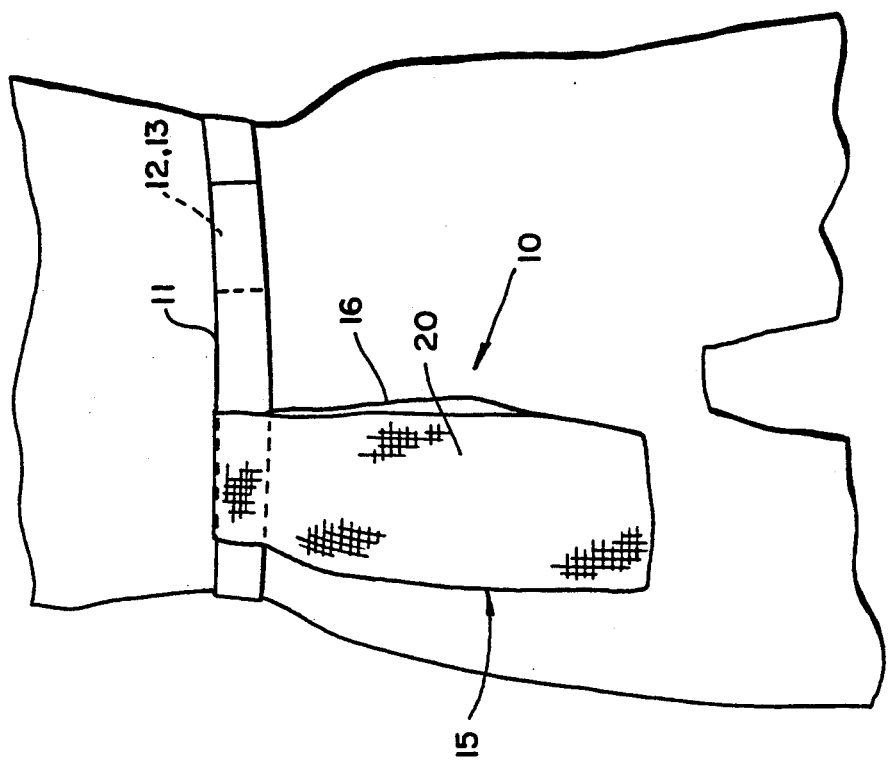
FIG. 1 is a somewhat schematic perspective view of the ostomy bag cover and support of the invention shown in operative position on the body of a user.
Figure 3:
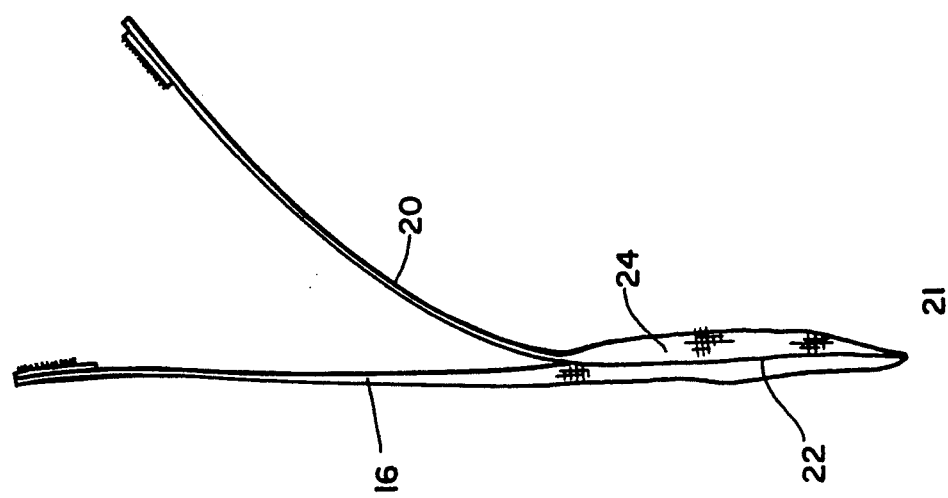
FIG. 3 is a side or edge view of the ostomy bag cover and support of the invention, showing the pocket at the bottom of the cover.
Figure 2:
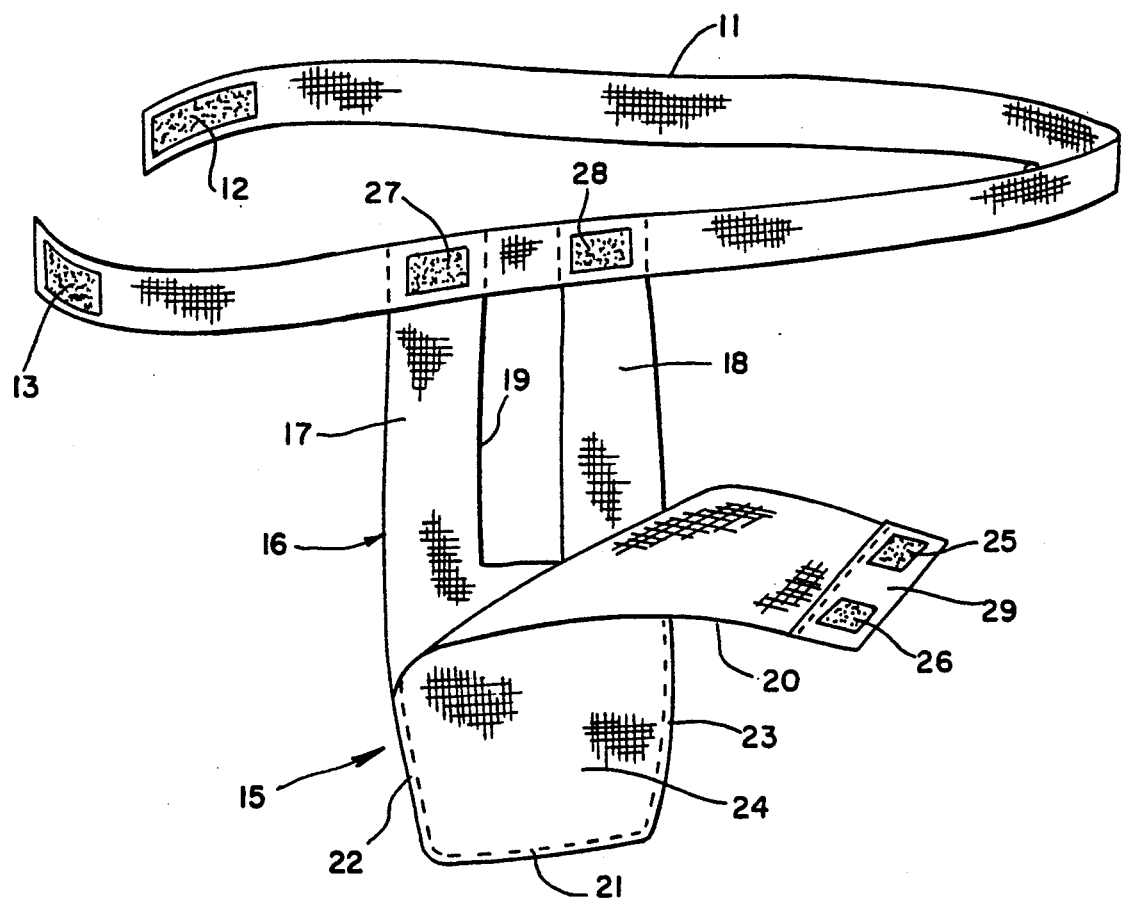
FIG. 2 is a perspective view of the ostomy bag cover and support of the invention, with portions in opened relationship.

Referring more particularly to the drawings, the ostomy bag cover and holder of the invention is represented generally at 10 in FIGS. 1-3, and comprises a belt or loop 11 of lightweight fabric material and having velcro fasteners 12 and 13 on the inside and outside surfaces thereof, respectively, at its opposite ends for adjustably securing the belt about the body of a user as shown somewhat schematically in FIG. 1. The velcro patches are preferably relatively elongate so that the belt will fit about the body of a range of different size persons.

A pouch 15 of lightweight fabric material is secured to the belt and comprises a back panel 16 bifurcated at its upper end to define a pair of spaced arms 17 and 18 defining a cut-out 19 therebetween for providing access of the ostomy bag to the stoma (neither shown herein), and a front panel 20. The upper ends of the arms 17 and 18 are stitched or otherwise suitably joined to the belt.

The front and back panels are joined along their lower ends and for a short distance upwardly along adjoining sides, at 21, 22 and 23, to define a pocket 24 in the lower end portion of the pouch. The front panel has a pair of velcro fasteners 25 and 26 on the upper inside corners thereof, for attachment to complemental fasteners 27 and 28 on the outer facing surface of the belt. As seen in FIG. 2, the upper end portion of the front panel is reinforced as at 29.

The fabric material of which the ostomy bag holder and cover of the invention is made is preferably cotton or a cotton blend, but other materials may be used as desired. Moreover, in the specific form of the invention shown and described herein, all exposed edges of the material, including the front and back panels, are hemmed, and the belt comprises a length of material folded over upon itself and stitched along one edge. The upper ends of the arms 17 and 18 are stitched between these folds.

In use, an ostomy bag is placed in the pocket 24 and the belt secured about the waist of the user. The bag is then attached to the stoma through the cut-out 19 and the front panel is secured in its up position by engaging the fasteners 25-28. When it is desired to examine or remove the bag, the front panel is folded downwardly, as shown in FIG. 2. It is not necessary to remove the entire holder and belt. The lightweight fabric material is absorbent, breathes, and is comfortable to wear, eliminating irritation to the skin of the patient as might be caused by contact with the ostomy bag itself, and is easy to use.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

I claim:

1. A self-belted ostomy bag holder and cover of lightweight fabric material for an ostomy patient for holding and covering an ostomy appliance without attachment thereto, consisting essentially of a inseparably connected unit of a belt or loop and a pouch unconnected to the user's stoma, the belt or loop having adjustably securing and quick release means thereon for securing and releasing the belt or loop around the waist of the user, and the pouch inseparably connected to and suspended from the belt or loop for covering an ostomy bag to which it is sized, said pouch including a back panel attached at an upper end to the belt or loop and being a part thereof, and bifurcated at its upper end to form a pair of spaced-apart arms defining a cut-out therein sized to receive the ostomy bag and provide lateral access to a passage formed on the skin of the user, said arms joined at their upper ends to the belt and a front panel jointed at a lower end portion thereof to a lower portion of the back panel.

* * * * *